United States Patent [19]

Bernhardt

[11] Patent Number: 5,252,327

[45] Date of Patent: Oct. 12, 1993

[54] SOLUTIONS CONTAINING ANTIGEN AND ZINC HYDROXIDE OR IRON HYDROXIDE AS AN ADJUVANT AND PROCESSES FOR PREPARING SUCH SOLUTIONS

[75] Inventor: Dieter Bernhardt, Cölbe, Fed. Rep. of Germany

[73] Assignee: Behringwerke Aktiengesellschaft, Marburg/Lahn, Fed. Rep. of Germany

[21] Appl. No.: 419,105

[22] Filed: Oct. 10, 1989

[30] Foreign Application Priority Data

Oct. 12, 1988 [DE] Fed. Rep. of Germany ....... 3834729

[51] Int. Cl.$^5$ .............................................. A61K 39/00
[52] U.S. Cl. ....................................... 424/88; 424/89; 424/92
[58] Field of Search ............................... 424/88, 89, 92

[56] References Cited

U.S. PATENT DOCUMENTS 4,684,625 8/1987 Eppstein et al. ...................... 424/88
4,698,221 10/1987 Straub ................................... 424/89
4,981,684 1/1991 Mackenzie et al. ................... 424/88

FOREIGN PATENT DOCUMENTS 0108316 5/1984 European Pat. Off. .
1189340 4/1970 United Kingdom .

OTHER PUBLICATIONS

Gemant, *Biological Abstracts*, vol. 68(7), Ref. #41262, 1979.

*Primary Examiner*—Michael G. Wityshyn
*Assistant Examiner*—Abdel A. Mohamed
*Attorney, Agent, or Firm*—Finnegan, Henderson, Farabow, Garrett & Dunner

[57] ABSTRACT

A solution containing antigen and adjuvant for eliciting an immune response. The adjuvant comprises zinc hydroxide or iron hydroxide in an amount sufficient to enhance the immune response elicited by the antigen. A process for preparation of such a solution is also provided.

4 Claims, No Drawings

SOLUTIONS CONTAINING ANTIGEN AND ZINC HYDROXIDE OR IRON HYDROXIDE AS AN ADJUVANT AND PROCESSES FOR PREPARING SUCH SOLUTIONS

The invention relates to the use of zinc hydroxide or iron hydroxide gel and, where appropriate, a lecithin as adjuvant in antigen solutions and to antigen solutions containing such adjuvants.

Many antigens have such low immunogenicity that the immune response they induce after a single injection in an animal or a person is not measurable or only low. For this reason, adjuvants are added to the antigens in order to enhance the immune response of the body to an antigenic stimulus. This is why most inactivated viral and bacterial vaccines contain adjuvants. Mainly used in the said viral and bacterial vaccines are $Al(O)H_3$ and $AlPO_4$, singly or in combination, vegetable oils or mineral oils obtained from petroleum fractions, so-called medicinal pharmaceutical white oils of a composition which is not exactly defined. Freund's complete and incomplete adjuvant, consisting of the mineral oil ®Bayol F with and without extract of mycobacteria, is mainly employed in experimental vaccines.

These adjuvants can, however, display not only local reactions but also systemic side effects.

Besides the local and general tolerability of adjuvants, the following are of vital interest:
1. Their immunological mechanisms of action which they induce;
2. Their pharmacokinetics (biodegradability)

Re 1

Thus, it is generally known that. the mineral adjuvants ($Al(OH)_3$, $AlPO_4$) mainly induce only a humoral immune response, whereas the cellular immunity, which plays a dominant part in many viral infections, is stimulated only slightly or not at all.

The mineral oils, and particularly Freund's adjuvant, behave differently and are known to stimulate both the cellular and the humoral immune response.

Re 2

Adjuvants which have been used to date mostly remain at the injection site or are transported away and accumulate in other organs of the body, where they display their immunological and toxic effect, i.e. breakdown or excretion takes place only very slowly if at all. The adjuvants according to the invention, zinc hydroxide gel, iron hydroxide gel and lecithin behave differently. These undergo metabolism in the body. They are therefore less toxic.

It has been proposed in EP-A-0,108,316 (German Offenlegungsschrift 3,241,113) to use, besides other substances, compounds of zinc, specifically zinc salts as additives to vaccines.

However, it was found in pre-liminary tests on mice and guinea pigs that zinc salts BUCH as zinc chloride, zinc sulfate and zinc acetate or iron saltb such as iron-(III) chloride in aqueous solution have rather poor local tolerability and display no mieasurable adjuvant effect.

However, it has now been fouind, surprisingly, that zinc hydroxide and iron hydroxide gels, which can be obtained from appropriate salt solutions, have the following properties:

1. Zinc hydroxide and iron hydroxide gels have very good adsorbant properticis (virus and protein)
2. Zinc hydroxide and iron hydroxide gels have very good adjuvant propertiee;
3. Zinc hydroxide gel induces both humoral and cellular immunity.
4. Iron hydroxide gel induces mainly humoral immunity.
5. Zinc hydroxide and iron hydroxide gels have, by comparison with the adjuvants hitherto customary, a rather good local and general tolerability.
6. Addition of a lecithin to the zinc hydroxide and iron hydroxide gel further enhances the adjuvant effect of the hydroxide gels, further increases the local tolerability and further improves the for mulating characteristics of the vaccines.

Description of the process for the preparation of zinc hydroxide gel, iron hydroxide gel and lecithin 99 suspension by processes known per se:

Zinc hydroxide gel

1. Starting from $ZnCl_2$, zinc acetate $\times 2H_2O$, $ZnSO_4 \times 7H_2O$ —preparation of a 0.1 M solution in distilled water.
2. Starting from zinc carbonate hydroxide—preparation of a 0.1 M solution in distilled water by addition of 5 N HCl.
3. Sterile filtration of the zinc salt solution (0.2 $\mu$ membrane filter).
4. Addition, under sterile conditions and while stirring, of 10 N NAOH or 10 N KOH until a pH of 6.0–7.8 is reached.
5. The precipitated zinc hydroxide gel can be further homogenized by OUltraturrax treatment.

The starting zinc salts used here are only by way of example. It is likewise possible to prepare zinc hydroxide gels easily by the debcribed processes from the other zinc salts (including zinc oxide) too. It is equally possible to prepare a zinc hydroxide gel while monitoring the pH directly in an antigen suspension. If non-sterile conditions are used, not sterile zinc salt solutions, the gel can be autoclaved at 120° C. for 20 min.

Iron hydroxide gel

The preparation of iron hydroxide gel was carried out in a manner analogous to the preparation of zinc hydroxide gel. Used as starting salt solution was 0.25 M $FeCl_3$ in distilled water.

Preparation of a 20 % strength lecithin 99 suspension
1. 20 g of lecithin are suspended in 100 ml of PBS, pH 7.2;
2. The suspension is autoclaved at 120° C. for 20 min;
3. After cooling, the suspension is homogenized;
4. pH of the suspension is adjubted to 7.0–7.8 with 10 N NAOH.

These gels and, where appropriate, lecithin Buspension are added to an antigen solution in the following amounts:

| Zinc hydroxide gel | 1–45% |
| --- | --- |
| Iron hydroxide gel | 1–45% |
| Lecithin suspension | 1–25% |

Suitable antigens are viral, bacterial, cellular, peptide and protein antigens.

The examples which follow explain the advantages of the inmunostimulators/adjuvants according to the invention.

EXAMPLES

Example 1

Aujeszky disease virus (AV) was grown in primary pig kidney cell cultures. After the cultures had undergone 100 % virus-specific destruction, the virus was harvested and purified by centrifugation and filtration. This was followed by AV inactivation with ethyleneimine. After the sterility and safety had been tested, 6 vaccines were prepared from this inactivated AV antigen.

The composition of the vaccines is listed in Table 1 hereinafter (data in ml):

TABLE 1

| Adjuvant/antigen | VACCINE | | | | | |
|---|---|---|---|---|---|---|
| | A | B | C | D | E | F |
| Al(OH)$_2$ 2% | 39.5 | | | | | |
| Saponin 10% | 0.5 | | | | | |
| Zn hydr. 0.1M gel | | 40 | | | 20 | 17.5 |
| Fe hydr. 0.25M gel | | | 40 | | 20 | 17.5 |
| Lecith. 99* 20% | | | | 40 | | 5.0 |
| AV antigen | 60.0 | 60 | 60 | 60 | 60 | 60.0 |
| Total: | 100.0 | 100 | 100 | 100 | 100 | 100.0 |

*Lecithin 99 (from Paesel GmbH & Co. Borsigallee 6, 6000 Frankfurt)

Each of these 6 vaccines was used to vaccinate 20 NMRI mice, weighing 18-20 g, with 0.2 ml. Before the vaccination and 4 weeks after the vaccination blood was taken from the animals to determine the neutralizing antibodies against Aujeszky virus. To determine the protection rate, the mice received 200 lethal doses of Aujeszky virus 4 weeks after vaccination.

The results of this experiment are listed in Table 2 hereinafter.

TABLE 2

| Vaccine | Neutral. antibody titer before vaccination | Neutral. antibody titer 4 weeks after vaccination | Protection rate (PD$_{50}$) |
|---|---|---|---|
| A | less than 1:2 | 1:12 | 2.0 |
| B | less than 1:2 | 1:86 | 25.0 |
| C | less than 1:2 | 1:60 | 4.0 |
| D | less than 1:2 | 1:10 | 1.5 |
| E | less than 1:2 | 1:110 | 30.0 |
| F | less than 1:2 | 1:204 | 65.0 |

It is clear from this experiment that zinc hydroxide and iron hydroxide stimulate higher antibody titers and protection rates against Aujeszky virus than does the standard adjuvant combination in vaccine A. The highest FIGURES are achieved with the new adjuvant combination (vaccine F) zinc hydroxide + iron hydroxide + lecithin 99.

EXAMPLE 2

Each of the vaccines from Example 1 was used for intraplantar vaccination of 3 guinea pigs, weighing 450-500 g, with 0.2 ml. The animals were examined each day up to day 28 after vaccination for swellings and other gross-pathological changes on the vaccinated foot in order to establish the intolerance of the vaccine. An intolerance score which increabes with the intolerance of the vaccine was calculated from the severity and duration of the grosB-Pathological changes. In addition, blood samples were taken from the animals before and 4 weeks after the vaccination in order to determine the neutralizing antibodies against Aujezsky virus.

The results of the experiment are summarized in Table 3.

TABLE 3

| Vaccine | Intolerance scores | Neutral. antibody titer before vaccination | Neutral. antibody titer 4 weeks after vaccination |
|---|---|---|---|
| A | 685 | less than 1:2 | 1:8 |
| B | 212 | less than 1:2 | 1:25 |
| C | 189 | less than 1:2 | 1:14 |
| D | 98 | less than 1:2 | 1:4 |
| E | 192 | less than 1:2 | 1:34 |
| F | 140 | less than 1:2 | 1:42 |

This experiment shows clearly that the adjuvants according to the invention are all considerably better tolerated than the standard adjuvant Al(OH)$_3$+saponin. The activity of zinc hydroxide and iron hydroxide gel, measured as the neutralizing antibody titer, is likewise better than that of the standard adjuvant which was also measured. The best activity together with good tolerability is achieved with the zinc hydroxide+iron hydroxide +lecithin 99 combination (vaccine F).

EXAMPLE 3

Vaccines A to F from Example 1 were each used to vaccinate 2 pigs, weighing 30-35 kg, with 2.0 ml s.c. The animals were examined each day up to week 3 after vaccination for swellings and gross-pathological changes at the injection site in order to determine the intolerance score for the two vaccines (see Example 2).

Blood was taken from the animals at the time of vaccination and 1, 2 and 3 weeks after vaccination to determine the neutralizing antibody titer against Auiezsky virus.

The results of the experiment are listed in Table 4:

TABLE 4

| Vaccine | Animal | Intolerance scores | Neutralis. antibody titer | | | |
|---|---|---|---|---|---|---|
| | | | before vacc. | 1 W after vacc. | 2 W after vacc. | 3 W after vacc. |
| A | 1 | 87 | *1:2 | *1:2 | *1:2 | 1:7 |
| | 2 | 96 | *1:2 | *1:2 | 1:4 | 1:12 |
| F | 3 | 19 | *1:2 | 1:5 | 1:17 | 1:32 |
| | 4 | 28 | *1:2 | 1:6 | 1:16 | 1:44 |

*denotes less than

This experiment clearly shows that the zinc hydroxide+ iron hydroxide + lecithin 99 adjuvant combination (vaccine F) is considerably better tolerated and more effective than the standard adjuvant Al(OH)$_3$, + saponin (vaccine A).

Example 4

Parainfluenza 3 (P,3) and IBR (infectious bovine rhinotracheitis virus) viruses were grown in primary calf kidney cultures. After the cultures had undergone 100 % virus-specific destruction, the virus was harvested and purified by centrifugation and filtration. This was followed by inactivation of both types of virus using ethyleneimine. After the sterility and safety had been tested, 2 vaccines were prepared with these inactivated antigens:

| Vaccine A contained: | |
|---|---|
| PI$_3$ antigen | 4.5 ml |
| IBR antigen | 4.5 ml |

-continued

| | |
|---|---|
| Al(OH)₃, 2% | 1.0 ml |
| Vaccine B contained: | |
| PI₃ antigen | 4.5 ml |
| IBR antigen | 4.5 ml |
| zinc hydroxide 0.1M | 0.4 ml |
| Fe hydroxide 0.25M | 4.0 ml |
| Lecithin 99, 20% | 0.2 ml |

Each of these vaccines was used to vaccinate 3 dogs with 1.0 ml s.c. and, 4 weeks thereafter, revaccinate them with the same dose of vaccine. All the animals were examined each day up to day 28 after vaccination and up to day 7 after revaccination for swellings and other gross-pathological changes at the injection site to assess the intolerance.

Blood samples were taken from the dogs before vaccination, 4 weeks thereafter and 1 week after the revaccination to determine the neutralizing antibodies against PI₃ and IBR virus.

The results are listed in Table 5.

TABLE 5

| Vaccine | Intolerance scores | | Neutralis. antibody titer against | | | | | |
|---|---|---|---|---|---|---|---|---|
| | 1st vacc. | 2nd vacc. | PI₃ before vacc. | IBR before vacc. | PI₃ 4 W after vacc. | IBR 4 W after vacc. | PI₃ 1 W after rev. | IBR 1 W after rev. |
| A  1 | 24 | 8+ | *1:2 | *1:2 | 64 | *1:2 | 3550 | *1:2 |
| 2 | 21 | 6+ | *1:2 | *1:2 | 42 | *1:2 | 2344 | *1:2 |
| 3 | 19 | 7+ | *1:2 | *1:2 | 18 | *1:2 | 1778 | 1:6 |
| B  4 | 8 | 5 | *1:2 | *1:2 | 86 | 1:12 | 3090 | 1:85 |
| 5 | 7 | 6 | *1:2 | *1:2 | 63 | 1:24 | 3090 | 1:97 |
| 6 | 4 | 4 | *1:2 | *1:2 | 74 | 1:8 | 3550 | 1:43 |

+Local reaction still present at end of experiment
*denotes less than

This experiment clearly shows that in dogb the adjuvant combination in vaccine B, zinc hydroxide + iron hydroxide + leicithin 99, is considerably better tolerated and more effective than the standard adjuvant Al(OH)3 in vaccine A. Good antibody titers against the IBR virus were detected in all 3 dogs which had been vaccinated with vaccine B. Of the animals which were vaccinated with vaccine A, only animal 3 had a low antibody titer.

I claim:

1. A process for the preparation of a solution containing an antigen and an adjuvant for eliciting an immune response comprising adding to an antigen solution an immunological adjuvant comprising a member of the group consisting of 1–45 % V/V iron hydroxide gel and 1–45 % V/V zinc hydroxide gel in an amount sufficient to enhance the immune response elicited by the antigen.

2. A process as claimed in claim 1, further comprising adding 1–25 % V/V of a lecithin.

3. A solution containing antigen and adjuvant for eliciting an immune response comprising, an antigen and an immunological adjuvant comprising a member of the group consisting of 1–45 % V/V zinc hydroxide gel and 1–45 % V/V iron hydroxide gel in an amount sufficient to enhance the immune response elicited by the antigen.

4. An antigen solution as claimed in claim 3, further comprising 1–25 % V/V of a lecithin.

* * * * *

UNITED STATES PATENT AND TRADEMARK OFFICE
CERTIFICATE OF CORRECTION

PATENT NO. : 5,252,327
DATED : October 12, 1993
INVENTOR(S) : Dieter Berhardt

It is certified that error appears in the above-indentified patent and that said Letters Patent is hereby corrected as shown below:

Claim 3, column 6, line 29, after "containing" insert --an--.

Claim 3, column 6, line 29, before "adjuvant" insert --an--.

Claim 3, column 6, line 30, after "comprising" delete --,--.

Signed and Sealed this

Thirteenth Day of September, 1994

*Attest:*

BRUCE LEHMAN

*Attesting Officer*     *Commissioner of Patents and Trademarks*